(12) United States Patent
McBean et al.

(10) Patent No.: US 7,367,958 B2
(45) Date of Patent: May 6, 2008

(54) METHOD OF USING POWERED ORTHOTIC DEVICE

(75) Inventors: John M. McBean, Boston, MA (US); Kalais N. Narendran, S. Burlington, VT (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/737,416

(22) Filed: Apr. 19, 2007

(65) Prior Publication Data

US 2007/0191743 A1 Aug. 16, 2007

Related U.S. Application Data

(63) Continuation of application No. 10/718,913, filed on Nov. 21, 2003.

(60) Provisional application No. 60/428,196, filed on Nov. 21, 2002.

(51) Int. Cl.
*A61F 5/00* (2006.01)
(52) U.S. Cl. .............................. 602/16; 602/20; 602/23
(58) Field of Classification Search ................... 602/5, 602/16, 18, 20, 23, 26; 128/877–879, 882
See application file for complete search history.

(56) References Cited

U.S. PATENT DOCUMENTS

| | | | |
|---|---|---|---|
| 3,631,542 A | | 1/1972 | Potter |
| 3,769,636 A | * | 11/1973 | Friedman ..................... 623/24 |
| 4,030,141 A | | 6/1977 | Graupe |
| 4,209,860 A | | 7/1980 | Graupe |
| 4,650,492 A | | 3/1987 | Barkhordar et al. |
| 4,685,925 A | | 8/1987 | Childress et al. |
| 5,112,296 A | * | 5/1992 | Beard et al. .................. 602/28 |
| 5,282,460 A | | 2/1994 | Boldt |
| 5,466,213 A | | 11/1995 | Hogan et al. |
| 5,685,830 A | | 11/1997 | Bonutti |
| 5,800,561 A | | 9/1998 | Rodriguez |
| 5,835,005 A | * | 11/1998 | Furukawa et al. .......... 370/400 |
| 5,853,005 A | | 12/1998 | Scanlon |
| 5,888,212 A | * | 3/1999 | Petrofsky et al. ............. 623/24 |
| 5,888,213 A | | 3/1999 | Sears et al. |
| 5,954,621 A | | 9/1999 | Joutras et al. |

(Continued)

OTHER PUBLICATIONS

Abul-Haj, et al., "Functional Assessment of Control Systems for Cybernetic Elbow Prostheses-Part II: Application of the Technique", 1990, IEEE Transactions on Biomedical Engineering, vol. 37, No. 11, pp. 1037-1047.

(Continued)

*Primary Examiner*—Michael A. Brown
(74) *Attorney, Agent, or Firm*—Bromberg & Sunstein LLP (57) ABSTRACT

A method of providing rehabilitation movement training for a person suffering from nerve damage, stroke, spinal cord injury, neurological trauma or neuromuscular disorder in attempting to move a body part about a joint using a powered orthotic device includes sensing at least one electromyographic signal of a muscle associated with motion about the joint, applying in a first direction with respect to the joint a force having a magnitude that is a first function of the at least one sensed electromyographic signal, and applying in a second direction with respect to the joint a return force that is a second function of the at least one sensed electromyographic signal, wherein the second function differs from the first function.

17 Claims, 5 Drawing Sheets

U.S. PATENT DOCUMENTS

| | | | |
|---|---|---|---|
| 5,980,435 | A | 11/1999 | Joutras et al. |
| RE37,209 | E | 6/2001 | Hensley et al. |
| 6,379,393 | B1 | 4/2002 | Mavroidis et al. |
| 6,532,383 | B2 | 3/2003 | Maloney et al. |
| 6,616,579 | B1* | 9/2003 | Reinbold et al. ............. 482/91 |
| 6,660,042 | B1 | 12/2003 | Curcie et al. |
| 6,821,259 | B2 | 11/2004 | Rahman et al. |
| 6,880,487 | B2 | 4/2005 | Reinkensmeyer et al. |
| 6,944,496 | B2 | 9/2005 | Jeong et al. |
| 6,966,882 | B2 | 11/2005 | Horst |
| 6,969,365 | B2 | 11/2005 | Scorvo |
| 2002/0169402 | A1* | 11/2002 | Hatton et al. ................. 602/26 |
| 2003/0023195 | A1 | 1/2003 | Rahman et al. |
| 2003/0064869 | A1 | 4/2003 | Reinkensmeyer et al. |
| 2003/0212356 | A1* | 11/2003 | Scorvo ........................ 602/20 |
| 2005/0006980 | A1 | 1/2005 | Horst |
| 2006/0004307 | A1 | 1/2006 | Horst |

OTHER PUBLICATIONS

Benjuya, et al., "Hybrid Arm Orthosis", 1990, American Academy of Orthotics and Prosthetics, Journal of Prosthetics & Orthotics, vol. 2, No. 2, pp. 155-163.

Bowen, et al., "Surface EMG and Motor Control of the Upper Extremity in Muscular Dystrophy: A Pilot Study", 2002, IEEE Bioengineering Conf., pp. 289-290.

Brown, et al., "The Exoskeleton Glove for Control of Paralyzed Hands", 1993, IEEE, 1050-4729/93, pp. 642-647.

Downes, et al., "Distributed Control of an Electronically Powered Hip Orthosis", 1994, IEE Control Conference, pp. 24-30.

Fukuda, et al., "EMG-Based Human-Robot Interface for Rehabilitation Aid", Proceedings of the 1998 IEEE International Conference on Robotics and Automation, pp. 3492-3497.

Harwin, et al., "A Review of Design Issues in Rehabilitation Robotics with Reference to North American Research", IEEE Transactions on Rehabilitation Engineering, vol. 3, No. 1, Mar. 1995, 1063-6528/95, pp. 3-13.

Harwin, et al., "Criteria for Interfacing and Control of a Powered Upper Extremity Orthosis", RERC on Rehabilitation Robotics Applied Science and Engineering Laboratories, University of Delaware/A.I. DuPont Institute, Rehabilitation R&D Progress reports, 1995, vol. 33, p. 215.

Homma, et al., "An Upper Limb Motion Assist System, Experiments with Arm Models", Proceedings of the 1996 IEEE/RSJ Int'l Conference on Intelligent Robots and Systems, Victoria, B.C., Canada, Oct. 1998, 0-7803-4465-0/98, pp. 758-763.

Johnson, et al., "Development of a Mobility Assist For the Paralyzed Amputee, and Spastic Patient", 1996, IEEE; 0-7803-3131-1/96; pp. 67-70.

Kawamoto, et al., "Comfortable Power Assistant Control Method for Walking Aid by HAL-3", 2000, IEEE SMC, TP1B2; 6 sheets.

Kawamura, et al., "A Design of Motion-Support Robots for Humans Arms using Hexahedron Rubber Actuators", 1997, IROS, IEEE, pp. 1520-1526.

Kazerooni, "Stability and Performance of Robotic Systems Worn by Humans", University of Minnesota, Mechanical Engineering Dept., May 13-18, 1990 IEEE, vol. 1, pp. 558-563,.

Kiguchi, et al., "An Exoskeletal Robot for Human Elbow Motion Support-Sensor Fusion, Adaptation, and Control", 2001, IEEE Transactions on Systems, Man, and Cybernetics-Part B; Cybernetics, vol. 31, No. 3, Jun. 2001, 1083-4419/01, pp. 353-361.

Kiguchi, et al., "An Exoskeleton System for Elbow Joint Motion Rehabilitation", Proceedings of the 2003 IEEE/ASME International Conference on Advanced Intelligent Mechatronics (AIM 2003), pp. 1228-1233.

Krebbs, et al., "Robot-Aided Neurorehabilitation in Stroke: Three-Year Follow-Up", 1999, Int'l Conference on Rehabilitation Robotics, pp. 34-41.

Krebs, et al., "Increasing Productivity and Quality of Care: Robot-Aided Neuro-Rehabilitation", Journal of Rehabilitation Research and Development, vol. 37, No. 6, Nov./Dec. 2000, pp. 1-4.

Krebs, et al., Robot-Aided Neuro rehabilitation, 1998, IEEE Transactions on Rehabilitation Engineering vol. 6, No. 1, Mar. 1998, pp. 75-77.

Lee, et al. Power Assist Control for Walking Aid with HAL-3 Based on EMG and Impedance Adjustment around Knee Joint 2002, IEEE/RSJ Int'l Conf. on Intelligent Robots and Systems, EPFL, Lausanne, Switzerland, Oct. 2002; 2002 IEEE; 0-7803-7396-7.02 pp. 1499-1504.

Lee, et al., "A New Exoskeleton-type Masterarm with Force Reflection: Controller and Integration", 1999, IEEE/RSJ International Conference on Intelligent Robots and Systems, pp. 1438-1443.

Lum, et al., "A Robotic System for Upper-Limb Exercises to Promote Recovery of Motor Function Following Stroke", ICORR '99: International Conference on Rehabilitation Robotics, Stanford, CA, pp. 235-239.

Lum, et al., "Quantification of Force Abnormalities During Passive and Active-Assisted Upper-Limb Reaching Movements in Post-Stroke Hemiparesis", 1999, IEEE Trans on Biomed, vol. 46, No. 6, pp. 652-662.

Lum, et al., "Robotics Assist Devices for Bimanual Physical Therapy Preliminary Experiments", 1993, IEEE Transactions on Rehabilitation Engineering, vol. 1, No. 3, pp. 185-191.

Morita, et al., "Basic Study on Rehabilitation Support System for Upper Limb Motor Function", 2002, IEEE AMC, pp. 127-132.

Parsons, et al., An Adaptable User Interface and Controller for a Rehabilitation Robotoc Arm, 1997, ICAR, pp. 919-923.

Popovic, et al., "Hybrid Assistance System-The Motor Neuroprosthesis", 1989, IEEE Transactions on Biomedical Engineering, vol. 36, No. 7, pp. 729-737.

Rabischong, et al., "Control and Command of a Six Degrees of Freedom Active Electrical Orthosis for Paraplegic Patent", 1990, IEEE International Workshop on Intelligent Robots and Systems, pp. 987-991.

Reinkenmeyer, et al., "Guidance-Based Quantification of Arm Impairment Following Brain Injury: A Pilot Study", 1999, IEEE Transactions on Rehabilitation Engineering, vol. 7, No. 1, pp. 1-11.

Romilly, et al., "A Functional Task Analysis and Motion Stimulation for the Development of a Powered Upper-Limb Orthosis", 1994, IEEE Transactions on Rehabilitation Engineering, vol. 2, No. 3, pp. 119-129.

Rosen, et al.; "A Myosignal-Based Powered Exoskeleton System", 2001, IEEE Transactions on System, Man, and Cybernetics, Part A: Systems and Humans, vol. 31, No. 3, pp. 210-222.

Seliktar, et al., "Evacuation of Functional Capabilities of People with Muscular Dystrophy as Potential Users of Powered Orthoses", ASME Summer Bioengineering Conference, 1999, Jun. 16-20, Blue Sky Montana, 2 sheets.

Timoszyk, et al., "Robot-Assisted Locomotion Training after Spinal Cord Injury-Comparison of Rodent Stepping in Virtual and Physical Treadmill Environments", Department of Mechanical and Aerospace Engineering and Center for Biomedical Engineering, University of California, Irvine, 1990 IEEE International Conference, pp. 1-14.

Triolo, et al., "The Theoretical Development of a Multichannel Time-Series Myoprocessor for Simultaneous Limb Function Detection and Muscle Force Estimation", 1989, IEEE Transactions on Biomedical Engineering, vol. 36, No. 10, pp. 1004-1017.

Umetani, et al., "Skil Mate", Wearable Exoskeleton Robot, 1999, IEEE, 0-7803-5131, pp. IV984 to IV988.

Wiegner, Allen W., et al., "Design of a Triceps Orthosis for C5/C6 Quadriplegics" 0-7803-0785, 2/92, IEEE, pp. 1485-1486.

Wu, et al., "A Study of Neuromuscular-like Control in Rehabilitation Robot", Proceedings of the 1996 IEEE International Conference on Rotobics and Automation, Minneapolis, MN, 0-7803-2988-4/96, Apr. 1996, pp. 1178-1183.

Zardoshti-Kermani, et al., "EMG Feature Evaluation for Movement Control of Upper Extremity Prostheses", 1995, IEEE Transactions on Rehabilitation Engineering, vol. 3, No. 4, pp. 324-333.

* cited by examiner

METHOD OF USING POWERED ORTHOTIC DEVICE

CROSS REFERENCE TO RELATED APPLICATIONS

This patent application is a continuation of U.S. patent application Ser. No. 10/718,913 filed Nov. 21, 2003, which claims priority under 35 U.S.C. § 119(e) to U.S. Provisional Patent Application No. 60/428,196 filed Nov. 21, 2002, the disclosures of which are incorporated by reference herein in their entirety.

FIELD OF THE INVENTION

This invention relates generally to orthotic devices and more particularly to a powered orthotic device worn by a person about an existing limb or body part.

BACKGROUND OF THE INVENTION

Rehabilitation following severe neurological trauma, such as spinal cord injury or stroke, is difficult, but has been shown to provide useful results. Conventionally, physical therapy methods are used for such rehabilitation. However, these methods are labor intensive, often requiring one or more therapists to work with each patient. Conventional physical therapy methods include repetitive movement of a patient's limb or body part, with therapist assistance, in an attempt to strengthen muscles and improve lost muscle control associated with the limb or body part. This type of therapy is most often performed in a hospital. When the patient can effectively move the limb or body part so as to be able to care for themselves the patient may be discharged from the hospital.

Robot aided therapies have been developed as a way of cutting labor costs associated with rehabilitation. Conventional robot-aided therapy includes repetitive movement of a patient's limb or body part by means of a separate robot arm or the like, in much the same way that a physical therapist would move the patient's limb during conventional manual physical therapy. It has been shown that patients treated daily with additional robot-aided therapy during rehabilitation have improved motor activity at hospital discharge. There is evidence that improved recovery can result from more therapy, earlier therapy, and therapies that incorporate highly repetitive movement training. However, current robotic devices and therapies require the use of relatively large and expensive robots, practically suitable only for inpatient services at hospitals. Although the total labor cost may be reduced with robotic therapies, the therapy is still performed while the patient is an inpatient, still resulting in a relatively high cost.

With both robotic and manual therapies, a patient's progression thorough the therapy is essentially the same, i.e., they are subjected to a period of "rehabilitation" before being able to accomplish activities of daily living. The patient subjected to these therapies is generally not able to quickly return to normal activities outside of the inpatient environment.

For example, following an incomplete C4 (fourth cervical vertebrae) level spinal cord injury, a resulting symptom is almost complete loss of biceps muscle strength. Initial stages of rehabilitation simply involve the patient lifting their arm, in a repetitive fashion, with the assistance of a physical therapist. Once the patient has progressed far enough to lift their arm themselves, they can re-learn how to feed and care for themselves. A conventional robot-aided therapy merely provides the same repetitive lifting of the arm, but with a robot and without the therapist. Still, the patient must progress far enough to lift their arm themselves before leaving the hospital.

It will be appreciated that the patients described above have not lost a limb. Rather, the patients have lost strength in one or more limbs or body parts. Other types of injury, for which a patient has lost limb, are treated with prosthetic devices which replace the lost limb.

SUMMARY OF THE INVENTION

In accordance with the present invention, a powered orthotic device that is worn by and physically controlled by a patient suffering from neurological trauma, spinal cord or other nerve damage including stroke or neuromuscular disorder (e.g., muscular dystrophy, myotonias, myopathies or other congenital disorders) or a patient requiring general rehabilitation services or strength increase includes a brace to be couple to a desired body part, a sensor which senses an electrical signal at a muscle which is usually proximate the body part and an actuator coupled to receive a signal from the sensor and to provide a force having a magnitude which is proportional to a magnitude of the sensor signal. The sensor senses or otherwise determines a desired joint torque and the actuator applies a proportional amount of torque in parallel with the torque provided from the patient's own muscle. The sensor may include an integrated processor which utilizes signals produced by the sensor or alternatively the processor may be separate from the sensor. With this particular arrangement, a patient-worn which device provides the patient with an ability to control the limb or body part affected by spinal cord or other nerve or muscular damage more rapidly than previous therapy methods is provided. Since the powered orthotic device allows the patient to control an affected body part, the patient is able to more rapidly leave a hospital or other institution. Also, in cases where full rehabilitation is not possible, the patient can continue to use the powered orthotic device to perform activities of daily living. Also for patients with spasticity and tremor, it is possible to filter or extract the meaningful information from the user and reject the "noise" associated with the user's input, enabling them to smoothly move a spastic limb or body part. For patients that suffer from co-contraction it is possible to have the weaker, patient controllable, muscle group overpower the stronger, uncontrollable opposing muscle. Thus, in general the orthotic device could discern a patient's intent, despite co-contractions. The powered orthotic device of the present invention thus corresponds to a wearable, unencumbering exoskeleton that augments human physical capability by working in parallel with existing musculature. The device of the present invention both augments strength and can accelerate rehabilitation in people who have suffered from neurological trauma or neuromuscular disorders, or a general loss of strength.

In accordance with the present invention, a powered orthotic device for augmenting a person's muscular functionality includes a brace to be coupled to a body part of a person, about a joint. The brace includes at least one elastic brace strap for attaching the brace to the body part. An electromyographic (EMG) sensor is fixed within an elastic strap such that the sensor is coupled to at least one muscle of the person. In response to the person attempting to move the body part, the sensor senses a surface EMG signal of the muscle or muscles connected to the joint. The powered orthotic device determines a desired joint torque from the EMG signal, and provides a control signal in response thereto. An actuator is coupled to receive the control signal, and in response to the control signal, the actuator provides a force having a magnitude which is proportional to a magnitude of the control signal. The ratio of power delivered by the actuator to the mass upon which the actuator acts is selected such that the body part moves in a desired manner (e.g., in a smooth, controlled manner). When considering the mass upon which the actuator acts, it is necessary to take into account all of the elements contributing to the mass. In some embodiments in which the actuator is supported by the orthotic device and the user, the mass of the actuator itself should be considered.

In accordance with another aspect of the present invention, the powered orthotic device described above also includes a control means coupled to the actuator. The control means includes means for making a measurement of the joint torque and means for providing a feedback signal to the actuator to ensure an accurate application of the force provided by the actuator.

With this particular arrangement, the powered orthotic device can be controlled by a patient having spinal cord or other nerve damage, including stroke, by way of the EMG signal generated by the patient, to bend or otherwise move a joint or body part which the patient is otherwise unable to effectively move. In this way, the patient can be quickly rehabilitated to use their limb or body part, or can use the powered orthotic device for daily activities where rehabilitation is not fully possible.

In one embodiment, a wearable, powered, orthotic device that provides external assistance to enable a user to move in a desired motion is provided. The powered orthotic device provides increased strength for victims of degenerative neuromuscular conditions as well as other conditions. The device is worn by a user (e.g., in the form of a sleeve or a brace-type structure) and includes sensors which sense an electromyogram (EMG) signal generated by flexor and extensor muscles of a joint. The signals are processed to determine the user's desired joint torque and that information is provided to a control system. The control system adds a proportional amount of assistance to the user via a force provided to the user's limbs, for example, by a relatively light weight, actuator. This approach provides a relatively compact, inexpensive system. In some embodiments, all components of the system (including the actuator and power supply) are worn by the user. In this case, the device is fully portable. In such a fully portable embodiment, it may be preferable to provide the power supply as a relatively lightweight power supply. Relatively high mass components of the device can be mounted on the brace or a portion of the user's body in manner which does not impede the user's ability to move. Alternatively still, in another fully portable embodiment, relatively heavy components of the system (e.g., the actuator and power supply) may be worn by the user in a hip pack or other support structure. Such a support structure is preferably coupled to the user to support at least some components of the orthotic device while still keeping the orthotic device fully portable. At the same time, the support structure is provided so as not to add any additional mass (or a resistive force) to the limb or other body part to which the orthotic device is providing assistance. In other embodiments, an external power supply (e.g., the power supply from a wheelchair or other external device) can be used in which case portability depends upon the portability of the external power supply. Likewise, an actuator which is physically supported by an external structure other than the orthotic device or by the user (e.g., a wheelchair) can also be used. Again, in this case portability depends upon the portability of the external actuator.

By providing a device which is lightweight, portable, and wearable able, the device enables the wearer to carry on routine activities such as eating, personal hygiene, or controlling a wheelchair. One benefit is that the user will be able to use, and potentially retrain affected limbs following incidents such as stroke, incomplete spinal cord injuries, etc. The device also allows rehabilitation to be accomplished through the execution of daily tasks, decreasing the need for lengthy therapy sessions which are costly in terms in terms of effort, money and human resources.

In one embodiment device, portability and wearability are accomplished via a compact, high power density, high force actuator used with a lightweight structural brace. The actuator can be provided as an electric actuator, a hydraulic actuator, a pneumatic actuator of some combination thereof. In one embodiment, the device determines intended muscular force via surface electromyagram (EMG) sensors, force sensors, position sensors, velocity sensors or some combination thereof. A force estimator determines desired joint torque from the sensor signal. An output of the estimator can be scaled by a variable amount and an active feedback loop controls the amount of force applied to the joint by the actuator. Thus, the force exerted by the externally worn brace can be selected such that it is proportional to a function of the magnitude of the sensor signals. In one embodiment, the feedback loop relies on a relatively low impedance measurement of output torque to ensure an accurate application of force.

BRIEF DESCRIPTION OF THE DRAWINGS

The foregoing features of the invention, as well as the invention itself may be more fully understood from the following detailed description of the drawings, in which.

DETAILED DESCRIPTION OF THE INVENTION

Figure 1:
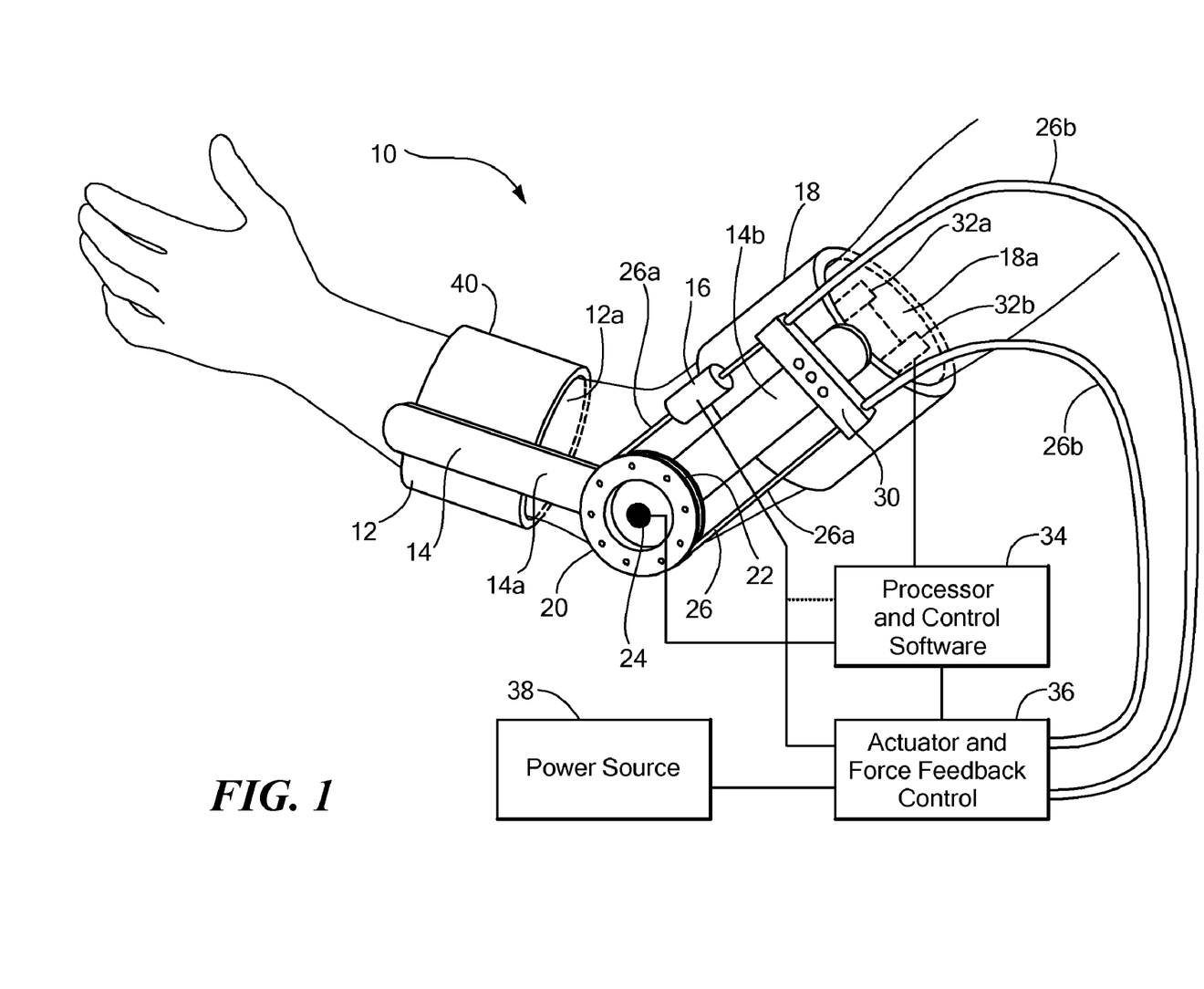
FIG. 1 is a diagrammatic view of a powered orthotic device.

Referring to FIG. 1, an exemplary powered orthotic device 10 is used by a patient who has lost the ability to normally bend an elbow, leg or other jointed body part is shown. It should be understood that although the powered orthotic device 10 is shown in FIG. 1 applied to an arm, the device (or a suitably adapted variant) can be used with a leg or other jointed body part.

In the embodiment shown in FIG. 1, a first attachment strap or cuff 12 can be worn on the forearm of the patient and a second attachment strap or cuff 18 can be worn about the biceps arm region of the patient. In one particular embodiment, the first and second straps 12, 18, respectively, can be elastic straps and can include fasteners (not shown), for example, hook and loop type fasteners, buttons, hooks, etc. . . . , which can allow the patient or caregiver to fasten and unfasten install and remove the first and second straps 12, 18 at will to facilitate wearing and removal of the device. In other embodiments, a zipper, buckle or friction-type strap attachment could be used. In still other embodiments, one or both of the attachment straps 12, 18 may be provided from an open or closed cell foam (e.g., a neoprene sleeve) having either an external or integrated hinge (i.e. a hinge mechanism integrated on, under or within the sleeve). In the case where an attachment strap is provided as a sleeve, a sensor can be placed under the sleeve. Such a sleeve would provide the function of holding the sensor in place while also holding other elements of the device 10 onto the body.

It should also be appreciated that one attachment device (e.g., an elastic strap) could be provided to attach the device 10 to a body while a different attachment device that was not used to attach the device to the body was used to hold sensors against the body. In this case, the device 10 would have an attachment portion (which may have an elastic characteristic) and would thus hold itself onto the body while a separate strap (also possibly having an elastic characteristic) would hold sensors in appropriate locations proximate or against a user wearing the orthotic device.

The patient wears the first and second straps 12, 18, respectively, about their elbow, the first strap 12 below their elbow, and the second strap 18 above their elbow, about their bicep.

In one particular embodiment, the first and second straps 12, 18 are coupled with a hinge mechanism 14 having first and second hinge portions 14a, 14b, respectively, which allow the first and second straps 12, 18 to move relative to each other in accordance with normal movement of the patient's elbow. In some embodiments, the hinge mechanism 14 can include adjustable physical stops or locks (not shown) which can limit the range of movement of the first strap 12 relative to the second strap 18 in order to avoid potential injury to the patient. The first and second straps 12, 18 together with the hinge mechanism 14, are herein referred to as a brace 40. In some embodiments, the person's joint may serve as the hinge, eliminating the necessity of a hinge mechanism on the brace.

A cable wheel 20 has a groove 22 adapted to receive a continuous cable 26. The continuous cable 26 passes around the cable wheel 20 within the groove 22. The continuous cable 26 is retained on the second strap 18 by a cable retainer 30. It will be appreciated that when the cable 26 is moved, the cable wheel 20 rotates, causing the first and second straps 12, 18 to move relative to each other in an angular motion resembling a bending elbow. The cable 26 can have an inner cable portion 26a, which, along certain portions of the cable 26, is surrounded by an outer cable jacket 26b, through which the inner cable portion 26a can slide. The cable 26 is received by an actuator 36 having force feedback control, which provides the movement of the cable 26. A power source 38, for example a battery, provides electrical power to the actuator 36. In one embodiment, the power source may correspond to the power source of a wheel chair in which the patient sits. The power source may be provided solely for the purpose of providing power to the orthotic device 10 or alternatively, the power source may be used to provide power to the orthotic device 10 as well as to other devices (e.g., the wheelchair drive system).

A pair of sensors 32a, 32b, collectively 32, are disposed to sense signals generated by a person wearing the orthotic device 10. In the exemplary embodiment shown in FIG. 1, the sensors 32 are provided as surface EMG sensors and thus it is important to have good contact between the sensor and the skin of the patient's body. To that end, the sensors 32 are coupled to an inner surface 18a of the second strap 18 so as to be in contact with a patient's skin against a biceps muscle, and/or against a triceps muscle, when the second strap 18 is worn by the patient.

It should be appreciated that in one embodiment, the sensors 32 are separate from the straps 12, 18 while in another embodiment, the sensors are coupled to or even provided as an integral part of the straps 12, 18. For example, the sensors may be fixed to a surface of the strap or the sensors may be integrated within the strap material. Alternatively, the sensors 32 can be attached directly to the body (e.g., by glue, other adhesive), or just held on by a strap (e.g., one of the cuffs 12, 18) without being fixed in it (i.e. the sensor can be held onto the body by contact force between the strap and the sensor and the body).

In one particular embodiment, the sensors 32 are provided as non-invasive electromyographic (EMG) sensors. Utilizing EMG sensors having relatively stiff electrodes (or more particularly relatively stiff electrode contact pads) contributes to the occurrence of artifacts due to motion of the person wearing the brace (referred to as "motion artifacts"). One reason motion artifacts occur is because relatively stiff electrode contact pads do not bend as a body part (e.g., an arm or leg) changes shape during motion. The occurrence of such motion artifacts can be reduced by wrapping an element having an elastic characteristic around the relatively stiff surface EMG electrodes. In one exemplary embodiment, this is accomplished by wrapping a sleeve or sleeve-type structure provided from a closed cell foam (e.g., neoprene) or other material having similar elasticity and strength characteristics around the electrode and wrapping the sleeve-electrode combination around a body part (e.g., an arm). By using a stiff but elastic element wrapped around relatively stiff surface EMG electrodes, the electrodes are less likely to disconnect from the surface of the skin of a person wearing the device which would result in an erroneous reading. The EMG sensors can be provided having built in amplifiers and filters. The above approach helps prevent both partial and full disconnects of electrodes/electrode pads.

In other embodiments, the sensors 32 may be provided as invasive electromyographic (EMG) sensors. In still other embodiments, the sensors 32 may be provided as a type of sensor other than an EMG sensor. In other embodiments, one or more of the sensors 32 may be provided as force sensors or another device that senses muscular contraction by determining change in radius of the limb, stiffness of the surface of the limb or the force which the limb exerts against an inside surface of the brace. In some applications, it may be desirable for the sensors 32 to receive input signals in addition to (or in some cases, in place of) EMG signals. For example, sensors which measure or sense joint angle, velocity or other parameters may be used in addition to (or in some applications in place of) EMG sensors. Such additional input may be desirable to provided additional functionality including but not limited to higher quality desired torque estimates, safer operation, application to a wider range of conditions, which may be desirable for treating certain conditions or certain types of patients such as stroke patients, for example.

The sensors can also be provided to measure signals from muscles not connected to the joint about which the device 10 is disposed. For example, the sensor could be disposed such that an action of flexing the left bicep muscle sends a signal to move the right elbow.

In summary, the sensors 32 may be provided as any type of invasive or non-invasive sensor capable of sensing information of the type required to allow appropriate control signals to be provided to a control system 36 to be described below. The particular type of sensor to select for use in a particular application depends upon a variety of factors including but not limited to the type of signal which must be detected, the characteristics of the signal to be detected, the reliability of the sensors, sensitivity of the sensors and cost of the sensors, the location on the body at which the sensors are placed, the proximity relative to the body at which the sensors must be placed, the size of the sensors, the available area on the body at which to place the sensors, the strength of an output signal provided by the sensors and the conditions of the environment in which the sensors will operate.

The sensors 32a, 32b are coupled to a processor 34 adapted to run control software. It should be appreciated that one or more of the sensors may be provided as wireless sensors which transmit sensor signals to the processor 34. In this case, the processor is adapted to receive wireless signal transmissions from the sensors. Alternatively, one or more of the sensors may be coupled to the processor via a conventional wired signal path.

The processor 34 may implement a control algorithm which produces a control signal which represents a force which is not directly proportional to the sensor signal. For example, it may be desirable to utilize a control methodology which takes into account non-linearities such as saturation (force limits).

The processor 34 may also implement a pre-programmed series of motions, either in response to one or more user inputs (e.g., signals sensed by the sensors 32) or independent of sensor signals. For example, if the user wants to keep their arm in its current position for an extended period of time (say, while drinking from a cup), they flex their arm quickly two times.

Load sensor or force sensor 16 (also referred to herein as a load cell or a joint torque sensor), adapted to sense tension upon the cable 26 (which is proportional to torque about the hinge assembly 14), is coupled to the actuator 36, forming a feedback loop. Optionally, the sensor 16 is coupled to the processor 34, also forming a feedback loop to the actuator 36. Sensor 16 may be selected such that it senses one or a variety of different forces including but not limited to tension, compression and torque.

A joint position sensor 24, coupled to the hinge assembly, is adapted to sense position of the hinge assembly 14 and to provide a rotation signal to processor 34. One of ordinary skill in the art will recognize that the joint position sensor 24 can be one of a variety of conventional rotation sensors and the tension sensor 16 can be one of a variety of conventional tension sensors. In the case where the orthotic device 10 does not include a hinge assembly (e.g., the person's joint itself functions as a hinge), the joint position sensor 24 can be disposed directly on the person's joint to sense or measure the position of the person's joint (or the position of limbs disposed on either side of the joint) and to provide a rotation signal to the processor 34. The joint position sensor can also be placed on the output shaft of the actuator if there is a known correlation between the movement of the actuator and joint.

The processor 34 is coupled to the actuator 36, controlling operation or the actuator 36, and therefore, relative motion of the first and second straps 12, 18, respectively. A power source, for example, a battery, provides power to the actuator 36. The actuator is selected having operating characteristics which are desirable for the particular application in which the orthotic device will be used. The particular type of actuator to select for use in a particular application thus depends upon a variety of factors including but not limited to the type of application, the reliability of the actuator, the sensitivity of the actuator, the cost of the actuator, the location at which the actuator will be placed (e.g., will the actuator be supported by the user in a fully portable system or supported by external means such as a wheelchair), the proximity relative to the body at which the actuator must be placed, the size of the actuator, the available area on the body at which to place the actuator, the strength of an output provided by the actuator and the conditions of the environment in which the actuator will operate.

In operation, when the patient attempts to move a body part (e.g., when the patient attempts to move their arm as shown in FIG. 1), signals (e.g., EMG signals) generated by the patient's muscles are sensed by the sensors 32a, 32b (e.g., EMG sensors). The signals are sent to the processor 34 which controls the actuator 36. In response to the signals the actuator moves the inner portion 26a of the cable 26, which moves the first strap 12 relative to the second strap 18. In the embodiment shown in FIG. 1 in which the orthotic device is disposed on an elbow, this causes the patient's arm to bend about their elbow. In this way, a patient having signals having a relatively small amplitude (e.g., EMG signals having a relatively small amplitude), in the vicinity of their biceps and/or triceps muscles, can still bend their elbow in response to the small EMG signal, with the assistance of the powered orthotic device 10. This operation is able to occur even when the signals measured from the patient are of insufficient strength (or frequency) to activate the patient's biceps and/or triceps muscles to move their arm. The above-described method of operation applies, of course, to any jointed body region (e.g., wrist, legs, ankles, etc. . . . ).

The amount of power delivered by the actuator 36 to the mass upon which the actuator 36 acts, takes into account all of the mass which must be moved by the force. In some embodiments, the mass of the actuator itself is considered in determining the necessary amount of power. For example, if the actuator is mounted on the brace itself, at a more distal location than the joint upon which it acts, then it is necessary to consider the mass of the actuator in determining the necessary amount of power needed for desired operation of the device.

In one particular embodiment, the actuator 36 comprises a motor adapted to move the cable 26. While an actuator mechanism comprising the cable wheel 20, the cable 26, the cable retainer 30, the actuator 36, and the power source 38 is shown, it should be understood that other actuator mechanisms can be used with this invention. For example, in another embodiment, an actuator (not shown), for example, a servo motor, stepper motor, hydraulic or pneumatic motor, can be coupled directly to the hinge mechanism 14, between the first and second portions 14a, 14b, without use of the cable 26. In yet another embodiment, a hydraulic actuator mechanism can be used and the cable 26 can be replaced with hydraulic lines. In yet another embodiment, a pneumatic actuator mechanism can be used and the cable 26 can be replaced with pneumatic lines. Also, in other embodiments, it is possible to provide an actuator mechanism which merely moves the first and second straps 12, 18 in one direction in accordance with a bending elbow, and passive springs or the like can move the first and second straps 12, 18 in accordance with a straightening elbow, or vice versa. It should also be understood that the actuator may be provided as a linear or a non-linear actuator.

It should also be understood that in one embodiment, the device 10 can be provided such that the actuator is physically located on the device while in another embodiment the actuator is not physically located on the device.

In one particular embodiment, the processor 34, the actuator 36, and the power source 38 can be coupled to a wheelchair, while the brace portion 40 is not attached to the wheelchair. This makes the powered orthotic device 10 lightweight and fully portable with the wheelchair. In another embodiment, the processor 34, the actuator 36, and the power source 38 can be coupled to a stationary rehabilitation center, along with the other parts of the powered orthotic device 10, and the patient can come to the rehabilitation center for therapy from time to time.

While two sensors 32a, 32b are shown, it should be appreciated that fewer than two or more than two sensors can be used. Also, while the sensors are shown to be coupled to the inner surface 18a of the second strap, in other embodiments, one or more sensors can be coupled to an inner surface 12a of the first strap 12, in place of or in addition to the sensors 32a, 32b. Also, although the sensors 32 are sometimes described herein as non-invasive EMG sensors, as described above, it should also be appreciated that sensors other than EMG sensors could also be used. For example, position, velocity and force transducers may be used in addition to or even in place of the EMG sensors. Furthermore, invasive sensors (e.g., needle-type EMG sensors) may be used in place of the non-invasive sensors (e.g., in place of surface EMG sensors).

By appropriate selection of materials and components from which the orthotic device is provided, a wearable, affordable, unencumbering exoskeleton that augments human physical capability by working in parallel with existing musculature is provided. Also the device can be made lightweight by appropriate selection of the brace materials. Also by selecting non-invasive sensors, the device itself is non-invasive.

It should be appreciated that although the device has been described above as a powered orthotic device for augmenting a person's muscular functionality, it should also be understood that the device can also be used for exercise, by working against the user's muscular force. As easily as the system can assist or augment a person's muscular functionality, the device could also be made to provide resistance by negating the control signal to the actuator. Thus, in this application, instead of providing an external force that is proportional and in the same direction as a person's muscular force, the device could provide a force that would be proportional and in an opposing direction to a person's muscular force. In other embodiments, the device could provide resistance to user motion that is not necessarily proportional to the sensor signals (for example, a brace that resists motion based on speed, or position, or the trajectory history of the user).

It should also be appreciated that the brace portion of the device may be provided in the form of a splint or a sleeve or other structure rather than a conventional brace-type structure. For example, in some embodiments, straps 12 and 18 may provide the brace. Thus, the orthotic device can be provided as a device which utilizes sensors (e.g., EMG sensors to sense signals used to provide control signals), which is constructed from new components (rather than being a modification of a pre-existing brace) and which provides a proportional force in parallel (or against) a person's muscular force.

It should also be appreciated that in some embodiments, the portions of the device which attach to a person's body (e.g., straps 12, 18 in FIG. 1) are provided such that the device traverses at least one joint of the person. In some applications, however, it may be desirable to provide a device which spans two or more joints. For example, the device may span from above the shoulder all the way to the wrist, with at least one assistive actuator disposed proximate each joint. It should also be understood that the device may be provided such that it attaches to the body above and below a joint, but does not actually cover the joint. This is illustrated in FIG. 1, for example, by an embodiment in which the hinge 14 is omitted from the brace, leaving essentially cuffs 12, 18 around the upper and lower parts of the arm, with a pull cable between them and the natural elbow acting as a pivot).

It should also be understood that the device can also be adapted for use with animals (rather than humans).

The brace can also be constructed such that it attaches to more than one part of the body (e.g., shoulder, elbow and wrist) and it can also be provided such that it moves without significant input from the wearer. The brace can also be provided such that it moves upon some signal other than the person attempting to move. For example, in some applications, it may be desirable to provide a brace which moves in response to a person flexing a muscle. That is, a rather than trying to move a body part, a person could simply try to flex a muscle and in response to the flex action, the brace would apply force and cause motion.

In one particular embodiment, the device 10 determines a desired joint torque from an EMG signal measured by an EMG sensor. It should be appreciated, however, that the orthotic device 10 could also determine joint torque from an input other than an EMG signal. For example position, velocity, force, torque, time-history of trajectories (i.e. applying torque based on how active, or how the user has been moving the limb over the past 5 minutes . . . ), vibration (frequency of tremors) could all be used to provide the control signals.

While the description above describes the device such that in response to a sensor signal the actuator provides a force having a magnitude which is proportional to a magnitude of the sensor signal, it is not necessary for the device to operate in this manner. For example, in one embodiment, it may be desirable to provide a brace/actuator combination that acts without input from the sensors. For example, a spring return could be included on the triceps side of device 10 shown in FIG. 1.

Figure 2:
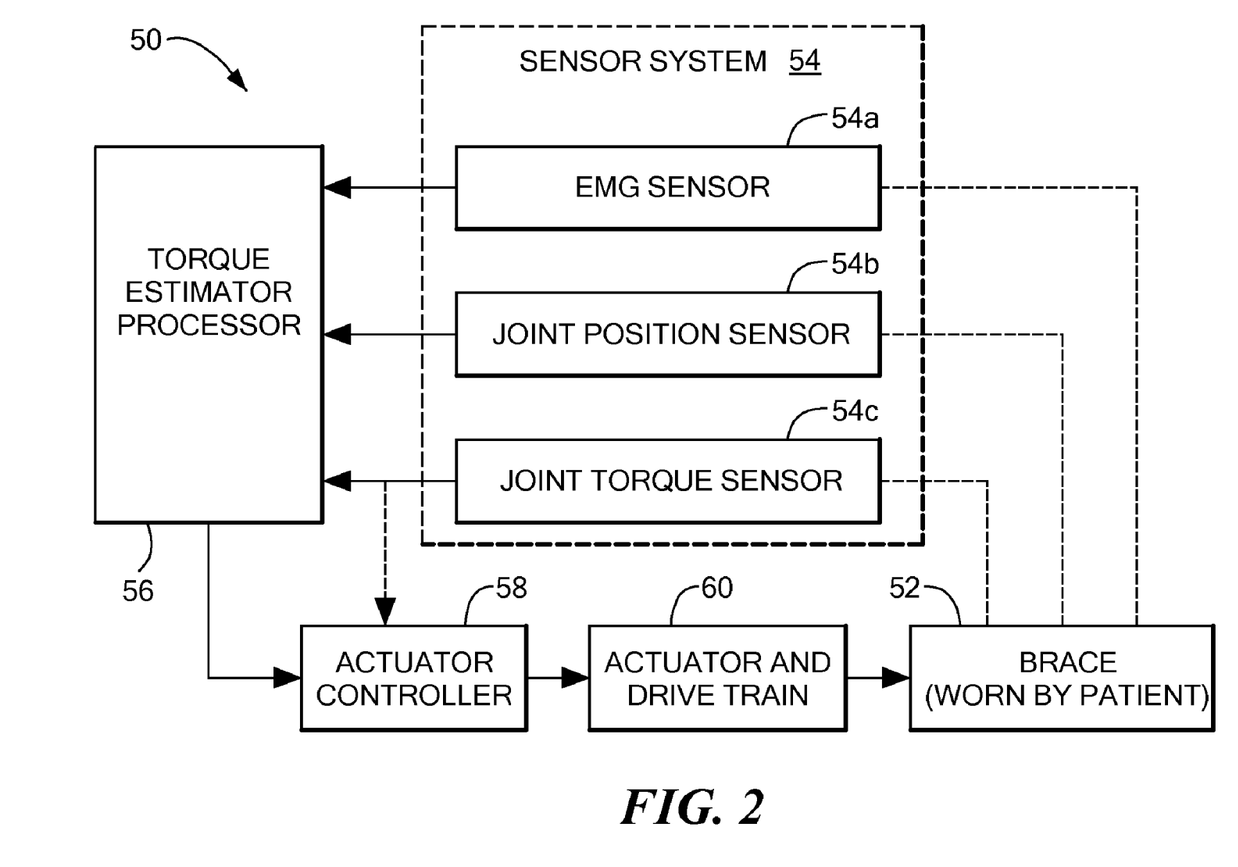
FIG. 2 is a block diagram of a powered orthotic device having a force feedback path.

Referring now to FIG. 2, a powered orthotic device 50 includes a brace 52 which is worn by a user. The brace 52 may, for example, be provided as the attachment cuffs 12, 18 or other structures described above in conjunction with FIG. 1. And, in the case where a person's joint or body part does not serve the function, the brace may optionally include the hinge mechanism 14 of FIG. 1.

A sensor system 54 includes sensors 54a-54c disposed on or proximate to the wearer of the brace 52 senses muscle movement or other characteristics of the brace wearer and provides signals to a torque estimator processor 56. In this exemplary embodiment, three sensors are shown with a first sensor 54a corresponding to an EMG sensor, a second sensor 54b corresponding to a joint position sensor and a third sensor 54c corresponding to a joint torque sensor which measures joint torque. Other types of sensors such as those described above in conjunction with FIG. 1 may also be used.

Also, although three sensors are shown in FIG. 2, it should be appreciated that as few as one sensor could be used. Alternatively, an unlimited number of sensors could be used. Thus, in some applications it may be desirable or even necessary to use as few as one sensor while in other applications, it may be desirable or even necessary to use a plurality of sensors. The particular number of sensors to use in any application may be selected in accordance with a variety of factors including but not limited to cost, amount of space available to mount the sensors, the type of input which is being measured on the wearer, activity level of the user, the limb on which the brace is being worn, the thickness of skin and fat covering the user's muscles, number of muscles being monitored, type of condition the brace is being used to treat.

As indicated by the dashed lines in FIG. 2, one or more of the sensors may optionally be attached to the brace 52. In such embodiments, the brace helps couple one or more of the sensors 54a-54c to the wearer of the brace 52. It should be noted, however, that it is not necessary for the sensor to be coupled to the brace 52.

A torque estimator processor 56 receives the signals provided thereto from the sensor system 54 and processes the senor signals to produce an estimate of the desired joint torque. The joint torque processor 56 then provides a joint torque estimate signal to an actuator controller 58.

The actuator controller 58 receives the signal from the torque estimator 56 and provides a control signal to an actuator and drive train assembly 60. The torque estimator processor provides a low power control signal, while the actuator controller outputs a high power driving signal to the actuator.

The actuator and drive train assembly 60 are coupled to the brace 52 being worn by the patient. The actuator and drive train assembly 60 may, for example, include the cable 26, the cable retainer 30, and the cable wheel 20 of FIG. 1. The actuator controller 58 and the actuator and drive train 60 may also include a combination of motors and force feedback control circuits. It should be appreciated that the processor 56, controller 58 and actuator/drive train 60 cooperate such that the actuator/drive train 60 provides to the user an applied force in a smooth and well-controlled manner. That is, the system components are selected having operating characteristics and are coupled in a manner which allows the system to achieve the desired effect of allowing the system to assist a user to move a desired body part in a controlled manner with a relatively smooth motion. That is, the system is provided having a compliance property (i.e. a property reciprocal to stiffness) which promotes smooth motion of a body part in a user. This effect is achieved by having the components of the system operating on various inputs to the system (as described above) until the output (which is a measure of the desired effect—e.g., smoothness of the motion or a characteristic of the actuator output signal) falls within an acceptable range of values. In one embodiment, a low backlash actuator and drivetrain (both designed in compliance), as well as compliance inherent in the system (e.g., by virtue of the coupling mechanisms used to couple moving components of the system) aid in smoothing out motions induced by the actuator. Force control, as opposed to pure position control, is also conducive to smooth motion, as compliance can be a part of the control process algorithm.

It should be appreciated that in the exemplary system of FIG. 2, three control loops are shown. A first control loop is associated with the surface EMG sensor 54a, a second control loop is associated with the joint position sensor 54b, and a third control loop is associated with the joint torque sensor 54c.

The joint torque sensor 54c can be coupled to the actuator controller 58, which includes force feedback control circuitry. Optionally, the joint torque sensor 54c can be coupled only to the processor 56 or optionally still the joint torque sensor 54c can be coupled only to the actuator controller 58.

It will be understood that a control loop is generally characterized by a variety of parameters, including but not limited to, bandwidth and gain. It would be desirable to provide gains associated with the control loops that can be adjusted in accordance with a particular patient. This is because each patient has spinal cord or other nerve damage that results in different magnitude EMG signals sensed by the powered orthotic device 50. Therefore, the processor 56 and/or the force feedback control of the actuator controller 58 can be provided with adjustable gain. The adjustable gain can be provided in a variety of ways, including but not limited to variable analog gain in the form of an adjustment knob or switches, and variable digital gain in the form of programmable firmware or switches. The particular gain and bandwidth selected to use in any particular application are selected in accordance with the details of the application.

It is generally desirable to filter analog sensor signals before they are converted to the digital domain for processing. In this way, signal to noise ratio can be improved and alias products generated in the digitization process can be minimized. Therefore, is desirable to provide filters to filter signals provided by the joint torque sensor 16, the joint position sensor 24, and the surface EMG sensor 32. The particular filter characteristics selected to use in any particular application are selected in accordance with the details of the application. It should be appreciated that the specific characteristics of the filters used in any application will vary widely based upon a variety of different factors including, but not limited to, the condition that is being treated, the physiology of the user and the type of use of the device (rehabilitation vs. activities of daily living).

It should be appreciated that the above described filtering and processing functions may be implemented in either in software or hardware or by using a combination of both software and hardware distributed between the sensor system 54 and the actuator 60.

In a practical case, the force feedback loop could be incorporated into a filtering and processing element, so the command signal provided to the actuator 60 is actually the command signal from the force feedback control loop.

It should also be appreciated that there is not necessarily a direct link between the sensors of the sensor system 54 and the actuator and drive train 60. All information can be passed through the processor 56 and controller 58. This means that the actuator 60 responds to commands from the processor 56 and controller 58, which are based upon the signals from the sensor system 54, but the exact relationship (linear, non-linear, twitch control, saturation limits, etc.) between the output signal provided by the actuator controller 58 (i.e., actuator command signal) and the output of the sensors (e.g., sensors 54a-54c) is unspecified because it will vary from treatment to treatment, patient to patient, etc.

Figure 3:
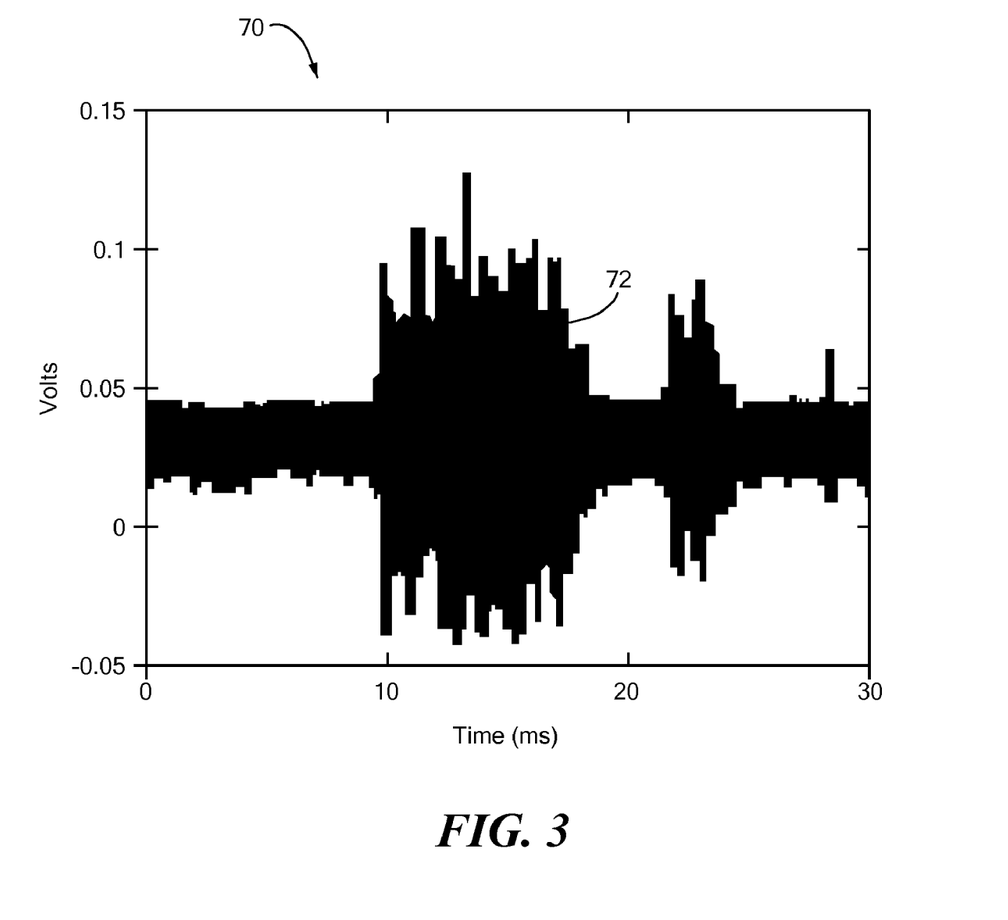
FIG. 3 is a graph showing a measured electromyographic (EMG) signal.

Referring now to FIG. 3, a measured EMG sensor signal 72 is provided by EMG sensors, for example, the EMG sensors 32 of FIGS. 1 and 2. The EMG sensor signal is shown on a graph 70 having an x-axis in units of milliseconds and a y-axis in units of volts.

The EMG sensor signal 72 was measured on the biceps of a patient having spinal cord damage and who is unable to lift their forearm. Even though the patient was not able to lift the weight of their own forearm, the EMG signal 72 has sufficient amplitude and a good signal to noise ratio. In addition, the repeatability of the EMG signal 72 was good, suggesting that the patient has a good degree of control over the small EMG signal 72, even though they lack strength.

The same experiment carried out on patients with varying levels of spinal cord injury (C3-C7), in addition to one patient with ALS (amyotrophic lateral sclerosis, a degenerative neurological disorder) has shown good results and repeatability.

Figure 4:
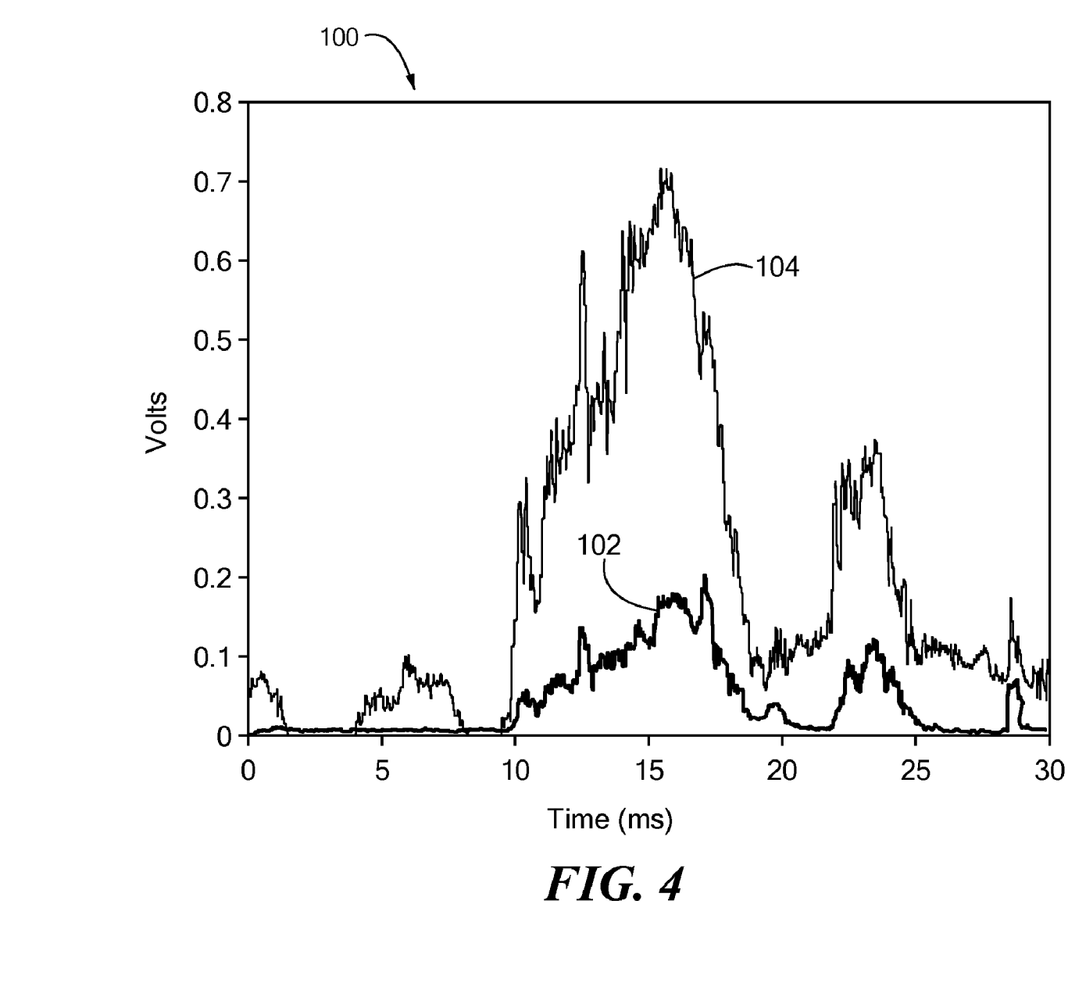
FIG. 4 is a graph showing a processed EMG signal and a resulting measured toque provided a powered orthotic device.

Referring now to FIG. 4, a graph 100 includes an x-axis in units of milliseconds and a y-axis in units of volts. A first curve 102 corresponds to a processed EMG signal, for example a processed version of the EMG signal 72 of FIG. 3. In one particular embodiment, the processing includes pre-filtering, rectifying, and low pass filtering the EMG signal to provide the processed EMG signal 102 as an amplitude envelope of the EMG signal 72. However, in other embodiments, other processing can be performed upon the EMG signal 72 to provide the processed EMG signal 102.

A curve 104 corresponds to a resulting torque applied to the powered orthotic device, as measured by a force transducer, for example the tension sensor 16 of FIG. 1. It can be seen that the shape of the curve 102 is similar to the shape of the curve 104, differing primarily in amplitude. When scaled to be of the same amplitude, it can be shown that the curve 102 differs from the curve 104 only by about one percent. Thus, the powered orthotic device achieves a torque 104 corresponding to the EMG signal 72 generated by the patient.

Figure 5:
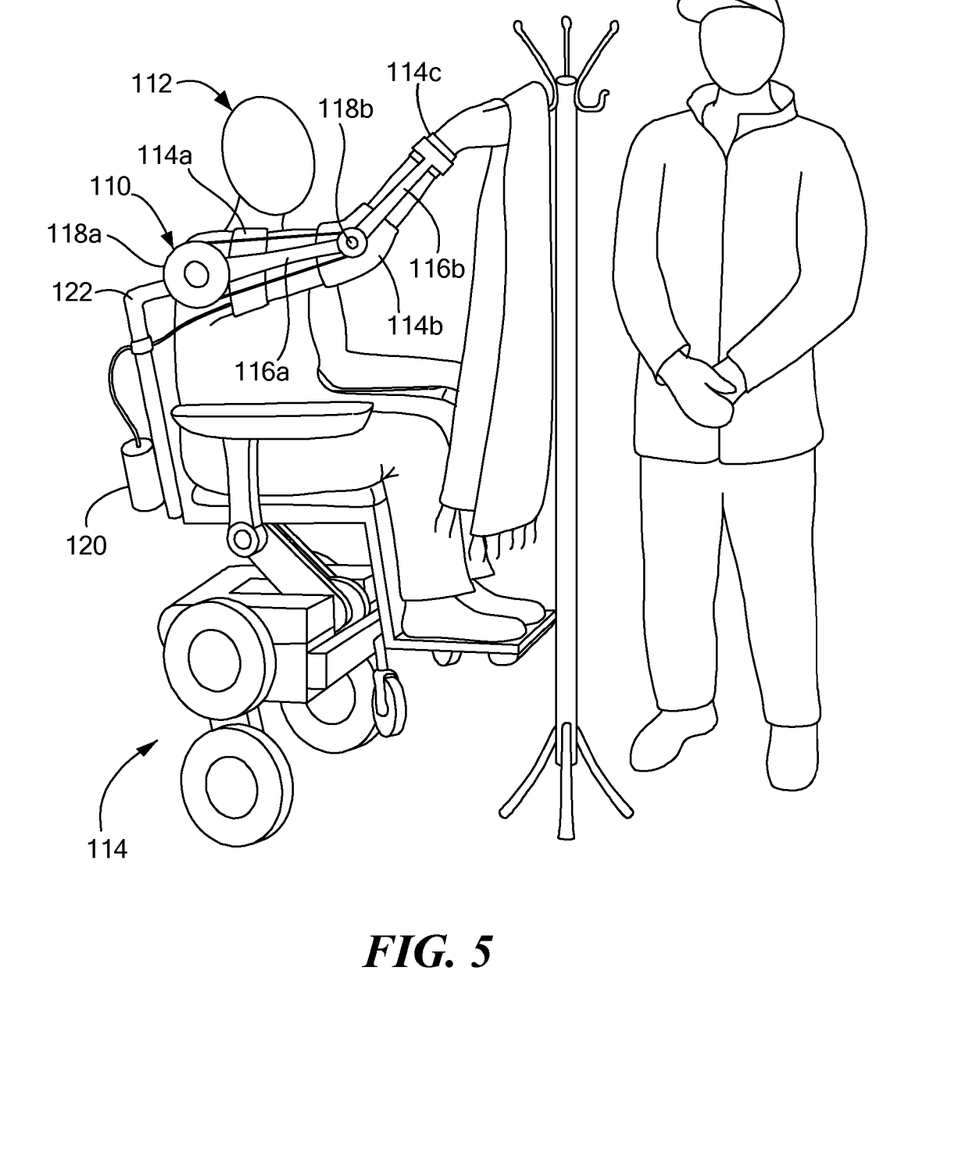
FIG. 5 is a diagrammatic view of a powered orthotic device worn by a user in a wheelchair.

Referring now to FIG. 5, an orthotic device 110 is disposed on a user 112. The device 110 is also coupled to a wheelchair 114 in which the user 112 is seated. The device includes sleeves or cuffs 114a, 114b, 114c disposed on an arm of the user 112. The cuffs 114a-114c are coupled via connecting structures 116a, 116b and joint structures 118a, 118b. The cuffs 114a-114c, connecting structures 116a, 116b and joint structures 118a, 118b together from an exoskeleton worn by the user 112.

An actuator 120 is coupled to the exoskeleton via cables disposed in a housing 122 while the weight of the actuator is supported by the wheelchair 114. By using cable drives and stiff but somewhat elastic cable housings, it is possible to position relatively heavy portions of the device 110 (e.g., the actuator and power supply) in locations in which the mass has a relatively small impact upon the magnitude of the forces which the actuator must provide to assist the user 112.

While the larger mass points of the system (e.g., the actuator and the power supply) are shown in FIG. 5 to be supported by an external structure (e.g., the wheelchair), it should be appreciated, that such relatively large mass points may also be worn by the user in a hip pack or other support structure attached to and supported by the user's body. Such support structures are preferably coupled to the user to support at least some components of the orthotic device while still keeping the orthotic device fully portable. At the same time, the support structure should preferably be provided so as not to add any additional mass (or a resistive force) to the limb or other body part to which the orthotic device is providing assistance in such a manner that substantially negatively impacts the user's ability to move the limb. It should be understood that a portion of the brace itself or the user's body itself may act as the support structure. That is the relatively high mass points may be mounted directly on the brace itself or the user's body itself Also, the drive system can be provided to allow convenient placement of the larger mass points (e.g., a power supply or actuator) in a hip pack or other support structure.

While the powered orthotic device has been shown and described in conjunction with a first and second strap 12, 18 (FIG. 1) worn about a patient's elbow, it should be appreciated that a similar powered orthotic device can be worn about any of the patient's movable joints or body parts to assist movement of those joints or body parts in response to EMG signals measured about those joints or body parts.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. A method of providing rehabilitation movement training for a person suffering from nerve damage, stroke, spinal cord injury, neurological trauma or neuromuscular disorder in attempting to move a body part about a joint using a powered orthotic device, the method comprising:
   sensing at least one electromyographic signal of a muscle associated with motion about the joint;
   applying in a first direction with respect to the joint, via an actuator having a rotational energy output coupled to the device at a location proximate to a portion thereof adjacent to the joint, a force having a magnitude that is a first function of the at least one sensed electromyographic signal; and
   applying in a second direction with respect to the joint a return force that is a second function of the at least one sensed electromyographic signal, wherein the second function differs from the first function.

2. A method according to claim 1, wherein applying in a first direction includes applying a force that has a magnitude proportional to the magnitude of the at least one sensed electromyographic signal.

3. A method according to claim 1, wherein applying in a first direction includes applying a force that is proportional to a first sensed electromyographic signal and is independent of a second sensed electromyographic signal.

4. A method according to claim 1, wherein applying in a second direction includes applying a return force that is a constant, independent of the at least one sensed electromyographic signal.

5. A method according to claim 1, wherein applying in a first direction includes applying a force that is a non-linear function of the at least one sensed electromyographic signal.

6. A method according to claim 1, further comprising:
   processing the at least one sensed electromyographic signal, wherein applying in the first direction includes applying a force having a magnitude that is a first function of the at least one sensed electromyographic signal after the at least one sensed electromyographic signal has been processed.

7. A method according to claim 6, wherein processing the at least one sensed electromyographic signal includes implementing a control algorithm for applying the force in the first direction so that the magnitude of the force is not directly proportional to the magnitude of the at least one sensed electromyographic signal.

8. A method according to claim 7, wherein the control algorithm takes into account non-linearities including saturation.

9. A method according to claim 7, wherein the control algorithm implements a pre-programmed series of motions.

10. A method according to claim 1, wherein applying in a second direction with respect to the joint a return force includes applying a spring return force.

11. A method of providing rehabilitation movement training for a person suffering from nerve damage, stroke, spinal cord injury, neurological trauma or neuromuscular disorder in attempting to move a body part about a joint using a powered orthotic device, the method comprising:
   sensing an electromyographic signal of a muscle associated with motion about the joint;
   applying in a first direction with respect to the joint, via an actuator having a rotational energy output coupled to the device at a location proximate to a portion thereof adjacent to the joint, a force having a magnitude related to a magnitude of the sensed electromyographic signal; and
   applying in a second direction with respect to the joint a return force in the absence of a sensed electromyographic signal of the muscle.

12. A method according to claim 11, wherein the force in the first direction has a magnitude proportional to the magnitude of the sensed electromyographic signal.

13. A method according to claim 11, further comprising:
   processing the sensed electromyographic signal, wherein applying in the first direction a force includes applying a force having a magnitude related to the magnitude of the sensed electromyographic signal after the sensed electromyographic signal has been processed.

14. A method according to claim 13, wherein processing the sensed electromyographic signal includes implementing a control algorithm for applying the force in the first direction so that the magnitude of the force is not directly proportional to the magnitude of the sensed electromyographic signal.

15. A method according to claim 14, wherein the control algorithm takes into account non-linearities including saturation.

16. A method according to claim 14, wherein the control algorithm implements a pre-programmed series of motions.

17. A method according to claim 11, wherein applying in a second direction with respect to the joint a return force includes applying a spring return force.

* * * * *

UNITED STATES PATENT AND TRADEMARK OFFICE
CERTIFICATE OF CORRECTION

PATENT NO.         : 7,367,958 B2
APPLICATION NO.    : 11/737416
DATED              : May 6, 2008
INVENTOR(S)        : John M. McBean and Kailas N. Narendran It is certified that error appears in the above-identified patent and that said Letters Patent is hereby corrected as shown below:

On title page, item 75 Inventors,
replace "Kalais N. Narendran"
with --Kailas N. Narendran.--

Signed and Sealed this

Eighth Day of July, 2008

JON W. DUDAS
*Director of the United States Patent and Trademark Office*